United States Patent [19]

Snyder

[11] 4,073,888

[45] Feb. 14, 1978

[54] CHLORINE DIOXIDE AND QUATERNARY AMMONIUM SALTS AS STERILIZING AGENTS

[75] Inventor: Martin Snyder, Elizabeth, N.J.

[73] Assignee: Pettibone Laboratories, Inc., New York, N.Y.

[21] Appl. No.: 552,517

[22] Filed: Feb. 24, 1975

Related U.S. Application Data

[63] Continuation-in-part of Ser. No. 480,335, June 18, 1974, abandoned, which is a continuation-in-part of Ser. No. 244,856, April 17, 1972, abandoned.

[51] Int. Cl.$^2$ .................. A01N 9/02; A01N 9/20; A01N 11/00
[52] U.S. Cl. ..................... 424/149; 424/329
[58] Field of Search .................. 424/149, 329; 106/15 AF; 252/21

[56] References Cited

U.S. PATENT DOCUMENTS

| 3,278,447 | 10/1966 | McNicholas | 424/149 |
|---|---|---|---|
| 3,280,137 | 10/1966 | Wakeman et al. | 424/329 |
| 3,968,250 | 7/1976 | Boucher | 424/333 |

FOREIGN PATENT DOCUMENTS 1,221,224  2/1971  United Kingdom.

OTHER PUBLICATIONS

Product News — Onyx Chemicals — "BTC—8—12 Octyl Dodecyl Dimethyl Ammonium Chloride", Jersey City, N.J.
Baird Chem. Industries, Inc. — "Product Information", "DI DAC—22", New York, N.Y.
Tanaka; Chem. Abst., vol. 45 (1951).
Hutton et al., Chem. Abst., vol. 64 (1966).
Ishidate et al., Chem. Abst., vol. 45 (1951).
Anthium Dioxcide; International Dioxide Inc., Bulletin No. 502, 4 pages, 9/1965.
Hueck et al., Applied Microbiology, vol. 14, No. 3, May 1966.
"Food Processing", Feb. 1975, pp. 18-20.
"Anthum Dioxcide", International Dioxide Inc., Bulletin No. 598, 6 pages, 9/1965.
"Cidex", Johnson & Johnson Co., 7 pages.

*Primary Examiner*—Allen J. Robinson
*Attorney, Agent, or Firm*—E. Janet Berry; Lawrence Rosen

[57] ABSTRACT

Compositions for cold, hard surface sanitization and sterilization solution having prolonged shelf-life which comprise chlorine dioxide and selected quaternary salts of the generic formula R', R" N(CH$_3$)$_2$X in which R' and R" are alkyl radicals each of which has at least 8 carbon atoms and the total carbon atoms of R' and R" equals 18-24 and X is a halide, and used therefor.

9 Claims, No Drawings

CHLORINE DIOXIDE AND QUATERNARY AMMONIUM SALTS AS STERILIZING AGENTS

This application is a continuation-in-part application of application Ser. No. 480,335, filed June 18, 1974 now abandoned, entitled "Sterilizing Agent", which is a continuation-in-part of Ser. No. 244,856, filed Apr. 17, 1972, entitled "Sterilizing Agent", now abandoned.

The invention relates generally to a composition of matter which is especially adapted for hard surface, cold sanitization and sterilization and cold solution sterilization especially for killing spores and more particularly, to aqueous compositions of matter containing chlorine dioxide and certain selected quaternary ammonium salts having the formula

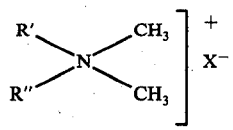

wherein R' and R" are alkyl radicals whose total carbon atoms number from 18 to 24, and preferably from 20–22. It is preferred that R' and R" be identical (symmetrical) but this is not necessary although each of the R' and R" radicals should have at least 8 carbon atoms. X is a chlorine, bromide, or any non-toxic non-interfering anion such as is known for the quaternary ammonium salts.

Certain methods are known for use in sanitization and sterilization in hospitals, operating rooms and the like. For sterilization it is necessary for compositions to possess the ability of killing spores as well as bacteria. For instance, one commercial sporicidal composition is a solution of glutaraldehyde which must be activated immediately prior to use and has only a 14-day recommended shelf-life after activation. However, methods using this composition require 10 hours to kill spores.

It is also known, for example, that chlorine dioxide can be used, either alone or in combination with other materials, especially those which function as stabilizers for the chlorine dioxide when it is in solution. For example, U.S. Pat. No. 2,082,146 describes the use of stabilized chlorine dioxide for treatment of water. The chlorine dioxide solutions are well known for their excellent bactericidal, fungicidal, and taste and odor control properties. Chlorine dioxide is known for inhibition of slime and algae for use in the milk and cheese industries, in the meat and poultry industries, for treatment of industrial wastes and effluents and in paper mills, swimming pools, animal pools and the like. Its non-toxicity and ready disappearance with no noxious by-products is a great advantage.

Chlorine dioxide alone in aqueous solutions, however, has been shown to be relatively ineffective as a cold sterilizing agent because it is not sporicidal, and this ineffectiveness also exists when stabilizers such as sodium carbonate, peroxides and chlorides and also when various materials are added to adjust the pH of the aqueous solutions of chlorine dioxide to the alkaline side of neutral. While the addition of KCl or other chlorides increases the efficiency of stabilized chlorine dioxcide, as cited in U.S. Pat. No. 3,585,147, this composition still does not kill spores.

In accordance with the present invention it has now been shown that only certain quaternary ammonium salts are effective when used with chlorine dioxide as sanitizing and sterilizing compositions. In the generic formula

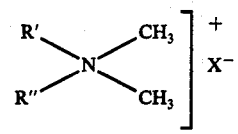

the carbon atoms in the alkyl radicals R' and R" should total 18–24, and preferably 20–22. The alkyl radicals R' and R" are preferred to be but not necessarily, symmetrical. X can be any non-interfering anion, and the halides, chloride or bromide are preferred. The quaternary salt need not be a pure compound, that is the R' and R" radicals can be a mixture of different molecules but each of the alkyl group should be at least C8, and if one is 8, then the other alkyl group should be at least 10.

While it is preferred that the alkyl group be the same, i.e. that the compound be symmetrical with respect to the alkyl groups, this symmetry is not essential for the effectiveness of the surface active agent used with the chlorine dioxide. The most preferred species is the compound in which $R_1$ and $R_2$ are straight chain radicals of $C_{10}$ to $C_{12}$ each. The other two radicals on the nitrogen atom are relatively low molecular weight and the dimethyl derivatives are much preferred; ethyl groups are also useful and propyl groups also but less so. Typical quaternary salts which have been found highly effective for the purposes of the invention are octyl-dodecyl dimethyl ammonium chloride, di-decyl dimethyl ammonium chloride, di-dodecyl dimethyl ammonium chloride, and the like. It is possible to use any combination of $C_8$ to $C_{12}$ alkyl radical such that the combined carbon atom content of the two radicals falls between $C_{18}$ and $C_{24}$. Such combinations include

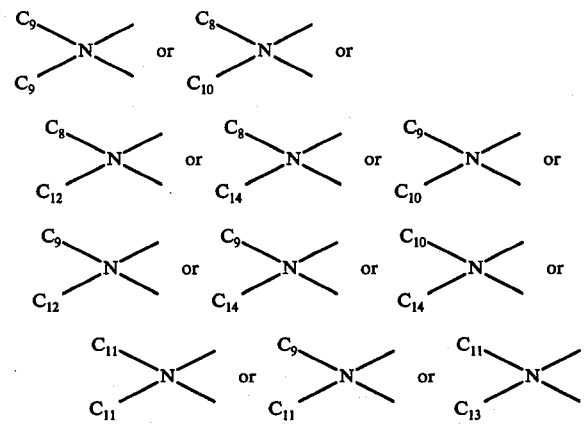

On the other hand, quaternary salts which are ineffective and whose structures do not conform to the skeletal configuration discovered to be necessary and above described include n-alkyl (50% $C_{14}$, 40% $C_{12}$, 10% $C_{16}$) dimethyl benzyl ammonium chloride, cetyl trimethyl ammonium bromide, hexadecyldimethyl benzyl ammonium chloride, lauric acid ester of colaminoformylmethyl pyridinium chloride, and alkyl ($C_{12}$, $C_{14}$, $C_{16}$, $C_{18}$) dimethyl benzyl ammonium chlorides.

The structure required for having the necessary effectiveness for forming useful combinations with the chlorine dioxide, are thus seen to be very specific and selective and these quaternary compounds cannot be predicted or judged as a class for these properties. The basic systems we tried were:

1. A di-alkyl quaternary structure which does not contain a benzene ring

between the nitrogen and the chloride.

(a) Example of straight chain quat

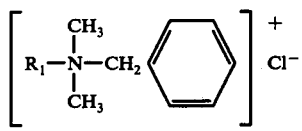

(b) Example of di-alkyl quat

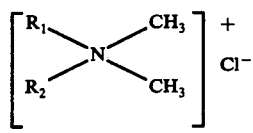

2. And a straight chain quat (see ex. (a))
3. We also tried a combination of two straight chain quats, an alkyl dimethyl benzyl ammonium chloride with alkyl dimethyl ethylbenzyl ammonium chloride:
Example of #3

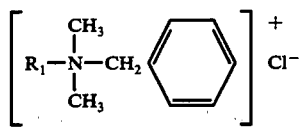

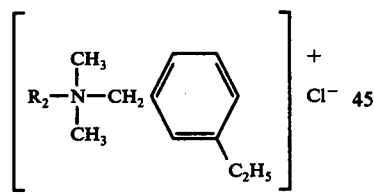

All of the above were tried with chlorine dioxide to kill spores, but only the dialky quaternary (see Example (b) above) proved successful.

In order to prepare the compositions the chlorine dioxide may be used either in pure form as well as a stabilized chlorine dioxide complex and in solution or suspension either aqueous or non-aqueous in concentrations of from 0.1% to 6.0%. It is preferred however to use the pure chlorine dioxide or its aqueous solution in concentrations of from 0.8% to 3.8%. It has been found generally necessary to employ one or more emulsifiers in small but effective amounts for the compositions of the invention. Those emulsifiers found especially useful are generally linear compounds which are primary alcohol ethoxylates having 12 moles of ethylene oxide and the primary alcohol portion being derived from $C_{12}$-$C_{15}$. The optimum range for use in this composition is that the primary alcohol contains from 5 to 12 moles of ethylene oxide, but from 3 to 15 moles are useful.

These compounds are non-ionic and this general class of compounds including such non-ionics as alkyl phenol ethoxylates also work well. Stabilizers are also advantageously employed in the compositions in small but effective amounts. Other materials, some of which may actually possess and show sanitizing properties on their own, may be included. For instance, chlorides such as sodium and potassium appear to exert an increased sanitizing effectiveness. It is only necessary that the additional materials not be toxic and not react with or cause deterioration of the compositions. Acidic materials cannot be added as they cause the elimination of gaseous chlorine dioxide from the composition.

The uses of this newly discovered combination of chlorine dioxide and the selected quaternary compounds have been found to be most unexpected and numerous. One of the most important and highly effective uses is as a so-called "cryoclave" agent or for use in hard surface sanitizing and sterilization for example in hospitals, kitchens, child care facilities, animal clinics, etc. They are also useful for cold solution sterilization, for example medical instruments, dental instruments, dialyzers, and any equipment that enters the human body.

The composition of the invention can also be effectively used in the paper industry, bottling plants, surgical scrub soaps, operating rooms, veterinary clinics, etc.

The products are also useful for all applications in which cold solution sterilization is known to be effective and is presently employed. It is, in fact, more effective than any of the presently known and used agents. The best and probably the only sterilization solution on the market:

1. Takes 10 hours to kill spores
2. Requires an activator
3. Is good for only 14 days after activation
4. Cost $9.00/gal. and is not diluted for use Our product:

1. Kills spores in 15–30 minutes
2. Does not require an activator
3. Is good for about 1 year
4. Cost about $9.00-$10.00/gal., but can be diluted 5-1 for use.
5. Is less irritating and less toxic to humans

EXAMPLE 1

Sporicidal Activity

An aqueous liquid consisting of a mixture of chlorine dioxide and didecyl dimethyl ammonium chloride prepared by:

| | |
|---|---|
| 1. Stablized chlorine dioxide solution (6.0%) | 60.0% |
| 2. Didecyl quat | 2.0% |
| 3. Neodol 25-12 (emulsifier) | 6.0% |
| 4. KCl | 0.4% |
| 5. Isopropanol | 5.0% |
| 6. Water | 26.6% |

Method:

1. Add chlorine dioxide, water, KCl, isopropanol, and Neodol 25-12.
2. Mix thoroughly for 10-15 minutes or till clear.
3. Add didecyl quat, and mix until a clear solution is obtained having 3.6% of the chlorine dioxide and 2.0% of the ammonium chloride compound was prepared and subjected to tests to ascertain its sporicidal activity for effectiveness as a cold instrument disinfection solution.

culture tube. Thirty minutes after completion of transfers, all cylinders were subcultured to fresh tubes of fluid thioglycollate medium.

All tubes were then placed into the incubator at 37° C. for 21 days, observing all tubes for growth during this period.

If no growth was observed after 21 days, all tubes were heat shocked for 20 minutes at 80° C. and reincubated for 72 hours at 37° C. The results were reported as + (growth) or − (no growth) values.

Table 1 below shows the good results obtained.

TABLE 1

Findings: Results of the Sporicidal Activity of Cold Instrument Disinfection Solution Undiluted and in Solution of 50% Against *Bacillus subtilis* at Specified Time Intervals

| Undiluted Specified Contact Time | Cold Instrument Disinfection Solution After 21 days of Incubation | | After Heat-Shocking and Reincubation | |
|---|---|---|---|---|
| | Subculture* | Resubculture | Subculture* | Resubculture |
| 2 Hours | 3− | 3− | 3− | 3− |
| 4 Hours | 3− | 3− | 3− | 3− |
| 6 Hours | 3− | 3− | 3− | 3− |
| 8 Hours | 3− | 3− | 3− | 3− |
| 10 Hours | 3− | 3− | 3− | 3− |
| 12 Hours | 3− | 3− | 3− | 3− |
| 50% Solution Specified Contact Time | After 21 days of Incubation | | After Heat-Shocking and Reincubation | |
| | Subculture* | Resubculture | Subculture* | Resubculture |
| 2 Hours | 3− | 3− | 3− | 3− |
| 4 Hours | 3− | 3− | 3− | 3− |
| 6 Hours | 3− | 3− | 3− | 3− |
| 8 Hours | 3− | 3− | 3− | 3− |
| 10 Hours | 3− | 3− | 3− | 3− |
| 12 Hours | 3− | 3− | 3− | 3− |

*3 Cylinders removed from dilution tube to individual subculture tubes
+ = growth
− = no growth The test organism used was Bacillus subtilis ATCC No. 19659 (72 hour macerated and filtered culture). The Sporicidal Test (4) used was that outlined in the Official Methods of Analysis of the Association of Official Analytical chemists, pages 64–65, with modifications. The cylinders were contaminated and dried 24 hours under vacuum as specified.

The disinfection solution was tested both undiluted and in solution of 50% concentration. 10 ml. of the test preparations were placed into each of six 25 × 150 mm tubes. These tubes were placed into a 20° C. water bath and permitted to come to the required temperature. Three contaminated cylinders were placed into each dilution tube. Each dilution tube was marked for a specific contact period of 2, 4, 6, 8, 10 and 12. At the end of the specific contact period, the three cylinders were removed from the disinfectant dilution tubes to subculture medium, placing only one cylinder into each sub- The solution tested showed satisfactory sporicidal activity against Bacillus subtilis at specified contact times of 2, 4, 6, 8, 10 and 12 hours.

EXAMPLE 2

Sporicidal Activity

Additional tests to those shown in Example 1 above were carried out using the same solution as that of Example 1 but in 20% and 25% solutions.

The test organism was Bacillus subtilis ATCC No. 19659 and the test procedure was that outlined in the Official Methods of Analysis of the Association of Official Analytical Chemists, pages 64–65, Eleventh Edition (1970).

The results obtained in these tests are set forth in Table 2 below.

TABLE 2

| CRYOCLAVE SOLUTION | | | | |
|---|---|---|---|---|
| 20% Solution Specified Contact Time | 21 Day Incubation | | Heat Shocked and Reincubated | |
| | Subculture | Resubculture | Subculture | Resubculture |
| ½ Hour | 20− | 20− | 20− | 20− |
| 1 Hour | 20− | 20− | 20− | 20− |
| Control | 10+ | | | |
| 25% Solution Specified Contact Time | 21 Day Incubation | | Heat Shocked and Reincubated | |
| | Subculture | Resubculture | Subculture | Resubculture |
| ½ Hour | 20− | 20− | 20− | 20− |
| 1 Hour | 20− | 20− | 20− | 20− |

TABLE 2-continued

CRYOCLAVE SOLUTION

| Control | 10+ |
|---|---|

+ = Growth
− = No Growth
The so-called "Control" used in the above Table 2 was carried out in order to test and establish the viability of the organism being tested.

Thus these control tubes are innoculated with the organism being tested. These control tubes also contain 2.5N HCl solution to prove the viability of the organism by its survival of contact with this acid. The importance of the control is only in tests where at least some of the tests show negative, since if the tests are positive the organism is obviously viable.

The tests showed that the composition was sporicidal against Bacillus subtilis in 20% and 25% solutions when used at both ½ hour and 1 hour contact times.

Comparative Sporicidal Tests on the Individual Components of the Cryoclave Solution of Example 1

A. Chlorine Dioxide (alone)

It was decided to test the possible sporicidal activity for comparative purposes of chlorine dioxide in dilutions of 1:10 and 1:25. The test organism was Bacillus subtilis and contact times of 2, 4, 6, 8, 10 and 12 hours were studied. Bacillus subtilis, ATCC No. 19659 was used. 72 hours macerated and filtered cultures were employed.

The Sporicidal Test (4) as outlined in the Official Methods of Analysis of the Association of Official Analytical Chemists, pages 64–65 with modifications were followed.

The cylinders were contaminated and dried 24 hours under vacuum as specified in the tests.

Chlorine dioxide was prepared in dilutions of 1:10 and 1:25. 10 m. of the prepared dilution was placed into each of six 25 × 150 mm tubes. These tubes were placed into a 20° C. water bath and permitted to come to temperature.

Three contaminated cylinders were placed into each dilution tube. Each dilution tube was marked for a specific contact period of 2, 4, 6, 8, 10 and 12 hours. After the specific contact periods the 3 cylinders were removed from the disinfectant dilution tubes to subculture medium, placing only one cylinder into each subculture tube. Thirty minutes after completion of transfers all cylinders were resubcultured to fresh tubes of fluid thioglycollate medium.

All tubes were placed into the incubator at 37° C. for 21 days, observing all tubes for growth during this period.

If no growth was observed after 21 days, all tubes must be heat shocked for 20 minutes at 80° C. and reincubated for 72 hours at 72° C. Results were reported as + (growth) or − (no growth) values.

Results of the Sporicidal Activity of Anthium Dioxcide (stabilized chlorine dioxide) I-10-0 in dilutions of 1:10 and 1:25 against Bacillus subtilis at Specified Time Intervals are shown in Table 3 below.

TABLE 3

| | AQUEOUS CHLORINE DIOXIDE | | | |
|---|---|---|---|---|
| Specified | Diluted 1:10 (10%) | | Diluted 1:25 (4%) | |
| Contact Time | Sub-culture* | Resub-culture | Sub-culture* | Resub-culture |
| 2 Hours | 3+ | 3+ | 3+ | 3+ |
| 4 Hours | 3+ | 3+ | 3+ | 3+ |
| 6 Hours | 3+ | 3+ | 3+ | 3+ |

TABLE 3-continued

| | AQUEOUS CHLORINE DIOXIDE | | | |
|---|---|---|---|---|
| Specified | Diluted 1:10 (10%) | | Diluted 1:25 (4%) | |
| Contact Time | Sub-culture* | Resub-culture | Sub-culture* | Resub-culture |
| 8 Hours | 2+, 1− | 3+ | 3+ | 3+ |
| 10 Hours | 2+, 1− | 3+ | 3+ | 3+ |
| 12 Hours | 2+, 1− | 3+ | 3+ | 3+ |

*3 cylinders removed from dilution tube to individual subculture tubes
+ = growth
− = no growth It was concluded from these tests that chlorine dioxide in dilutions of 1:10 and 1:25 when tested by the above described procedure does not show satisfactory sporicidal activity against Bacillus subtilis at the contact times of 2, 4, 6, 8, 10 and 12 hours. In fact, these tests show clearly the ineffectiveness of chlorine dioxide as a sporicide when used alone and chlorine dioxide is found to be a failure as a sporicide and for the purposes and objectives of the invention.

The product failed completely before the 21 day observation period.

In these tests, the most important consideration as to effectiveness is the time factor in the testing, showing that even at twelve hours contact time the sproicidal test was not passed at dilutions of 1:10 and 1:25.

B. Dialkyl (Didecyl) Dimethyl Ammonium Chloride (alone)

For further comparative purposes it was also decided to test the sporicidal activity of didecyl dimethyl ammonium chloride used alone and employing the bacteria and method described below.

The method of assay followed the Sporicidal Test, Methods of Analysis of the Association of Official Analytical Chemists, 11th Edition, 1970, Paragraph 4, 015–17 and the results are presented in Table 4 below.

TABLE 4

| Didecyl Dimethyl Ammonium Chloride | |
|---|---|
| Test Organism | ATTC# |
| Bacillus subtilis | 19659 |
| Apparatus | |
| Porcelain penicylinders (Fisher Scientific #7-907) | |
| Incubation Time and Temperature | |
| 21 Days at 37° C. | |
| Contact Time | |
| Ten minutes | |
| RESULTS: | |

| B. subtilis | | Number Positive |
|---|---|---|
| 1% solution | 1 2 3 4 5 6 7 8 9 10 | |
| Tube 1 | 0 0 0 0 0 0 0 0 0 0 | 0 |
| Tube 2 | 0 + + + + + + + + + | 9 |
| 0.4 % solution | | |
| Tube 1 | 0 0 0 0 0 0 0 0 0 0 | 0 |
| Tube 2 | + + + + + + + + + + | 10 |

SUMMARY: The test material showed poor sporicidal activity with B. subtilis.

In the above Table 4, Tube 1 is the original culture and Tube 2 is the subculture of Tube 1. In these tests, it is necessary that both Tubes 1 and 2 be 0 (negative) to show sporicidal activity and quite properly the Tube 2 in both tests are positive, showing that only a static effect and not a cidal effect was achieved, the static effect allowing the spore to grow once again.

The active ingredient in these tests was didecyl dimethyl ammonium chloride.

In the above Table 4, the identification of the 1% solution and 0.4% solution refers to the level of total quaternary compound being tested. The results show that at dilutions of 1% and 0.4% concentrations, this quaternary compound used alone was not sporicidal in any tests carried out.

To summarize and by comparison with the lack of sporicidal activity in the two ingredients used alone, in dilutions of 0.4% quaternary and 0.72 chlorine dioxide in the composition, i.e. the compositions of the invention were specifically sporicidal in many successive tests at 10 minutes contact time; and in one test it was found that the composition was sporicidal even at dilutions of 0.36% chlorine dioxide and 0.2 quaternary compound in 10 minutes contact time.

EXAMPLE 3

Additional and other dialkyl quaternaries having other and various structures were also employed in combination with chlorine dioxide to show that the synergistic effect of the combination of the components is in no way limited to the particular quaternary compound shown in Examples 1 and 2.

Additional tests were carried out on several samples of the composition of the invention (referred to as a cryoclave solution) and these are identified by structures as follows:

Sample 1 was made with $diC_8$ quaternary ammonium chloride and chlorine dioxide.

Sample 2 was made with $diC_{12}$ quaternary ammonium chloride and chlorine dioxide.

Sample 3 was made with a mixture of: 50% $C_8$ and $C_{10}$; 25% $diC_8$ and 25% $diC_{10}$ quaternary ammonium chloride and chlorine dioxide.

The structures of the quaternary ammonium chloride compounds used for making up the above samples 1, 2, and 3 are further clarified by the following structural formulas:

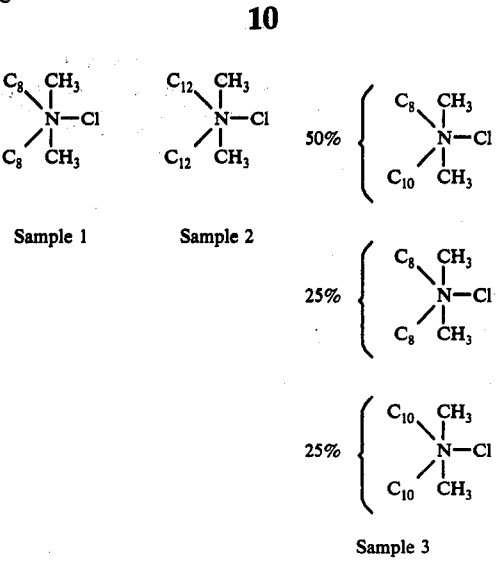

Sample 1  Sample 2

Sample 3

That the test organisms used were:

Bacillus subtilis — ATCC No. 19659 and
Staphylococcus aureus — ATCC No. 6538

The Sporicidal Test - Official Final Action as outlined in the Official Methods of Analysis of the Association of Official Analytical Chemists, pp. 64–65, Eleventh Edition (1970) was followed for all Sporicidal Testing; The Use-Dilution Method — Official Final Action as outlined in the same reference, pp. 61–63 was followed for testing against Staphylococcus aureus;

Samples identified as $diC_8$ quaternary (Sample 1), $diC_{12}$ quaternary (Sample 2) and Mixture (Sample 3) were effective in these Use-Dilution tests against Staphylococcus aureus at 50% and 100% concentrations; The sample identified as $diC_8$ quaternary (No. 1) was not sporicidal against Bacillus subtilis at 50% and 100% concentrations; and the samples identified as $diC_{12}$ quaternary (No. 2) and mixture (No. 3) were sporicidal against Bacillus subtilis at 50% and 100% concentrations;

That the details of the experiments are shown in Tables 5 and 6, presented hereinbelow.

TABLE 5

A. O. A. C. USE-DILUTION TEST ON CRYOCLAVE SPORICIDAL SOLUTIONS AGAINST *STAPHYLOCOCCUS AUREUS*

| Test Sample | Concentration | Active Ingredients quat.% | ClO₂% | No. Carriers Employed | 21 Day Incubation* Primary Subculture | Secondary Subculture |
|---|---|---|---|---|---|---|
| 1)diC₈quaternary compound & ClO₂ | a) 50% | 1.0 | 1.8 | 10 | 0/10 | 0/10 |
|  | b)100% | 2.0 | 3.6 | 10 | 0/10 | 0/10 |
| 2)diC₁₂quaternary compound & ClO₂ | a) 50% | 1.0 | 1.8 | 10 | 0/10 | 0/10 |
|  | b)100% | 2.0 | 3.6 | 10 | 0/10 | 0/10 |
| 3)Mixture - 50% C₈C₁₀quaternary 25% diC₈quaternary, 25% diC₁₀ quaternary compounds & ClO₂ | a) 50% | 1.0 | 1.8 | 10 | 0/10 | 0/10 |
|  | b)100% | 2.0 | 3.6 | 10 | 0/10 | 0/10 |

*No. positive/total no. specimens

TABLE 6

A. O. A. C. SPORICIDAL TEST ON CRYOCLAVE SPORICIDAL SOLUTIONS AGAINST *BACILLUS SUBTILIS* USING PORCELAIN CYLINDERS

| Test Sample | Concentration | Active Ingredients quat. % | $ClO_2$ % | No. Carriers Employed | 21 Day Incubation* Primary Subculture | Secondary Subculture |
|---|---|---|---|---|---|---|
| 1)di$C_8$quaternary compounds & $ClO_2$ | a) 50% | 1.0 | 1.8 | 10 | 10/10 | 10/10 |
|  | b)100% | 2.0 | 3.6 | 10 | 10/10 | 10/10 |
| 2)di$C_{12}$quaternary compound & $ClO_2$ | a) 50% | 1.0 | 1.8 | 10 | 0/10 | 0/10 |
|  | b)100% | 2.0 | 3.6 | 10 | 0/10 | 0/10 |
| 3)Mixture - 50% $C_8C_{10}$quaternary 25% di$C_8$, 25% di$C_{10}$ compounds & $ClO_2$ | a) 50% | 1.0 | 1.8 | 10 | 0/10 | 0/10 |
|  | b)100% | 2.0 | 3.6 | 10 | 0/10 | 0/10 |

Spores in 2.5 N HCl*
2 min. 2/2
5 min. 2/2
10 min. 2/2
20 min. 2/2

*No. positives/total no. specimens

To further substantiate the synergistic activity of the inventive compositions the following test is presented to show a sporicidal effectiveness at 10% of these compositions which level corresponds to 0.36% $ClO_2$ plus 0.2% quaternary compound. This test further substantiates the synergism which is obtained with the compositions of the invention.

| | |
|---|---|
| Sample: | An 8 oz bottle filled with a clear solution was tested. This sample was identified and labeled: "Cryoclave Sporicidal Solution", a mixture of 0.36% $ClO_2$ and 0.2% quaternary ammonium chloride. |
| Test Organisms: | *Bacillus subtilis*, ATCC No. 19659 |
| Method: | The Sporicidal Test-Official Final Action as outlined in the Official Methods of Analysis of the Association of Official Analytical Chemists, pages 64–65, Eleventh Edition (1970) was followed. |
| Findings: | See Table 7 below |
| Conclusions: | "Cryoclave Sporicidal Solution", in 10% Solution when tested as indicated was sporicidal against *Bacillus subtilis*, after 10, 15 and 20 minutes of contact time. |
| Findings: | "Cryoclave Sporicidal Solution" in 10% Solution |

TABLE 7

| Specified Contact | No. of Tubes Showing Growth After | |
|---|---|---|
|  | 21 Days of Incubation | Heat Shocking and Resubculture |
| 10 min. | 0/30 | 0/30 |
| 15 min. | 0/30 | 0/30 |
| 20 min. | 0/30 | 0/30 |

Test Spores in 2.5 N HCl (Organism Control)
2 min. 2/2
5 min. 2/2
10 min. 2/2
20 min. 2/2

Note: Number of positives/total number of specimens

In order to show further sporicidal activity of the invention compositions, other bacterial spores were tested and in these cases also, the compositions proved to be highly effective when used at the same concentration levels as disclosed in the specification and defined in the concentration ranges of the claims. The two test organisms were Clostridium Sporogenes and Clostridium Perfringens. The tests are described and the data resulting therefrom are presented below.

| | |
|---|---|
| Sample: | An 8 oz. glass bottle containing a clear light yellow liquid was tested. The sample was identified and labeled as Cryoclave Sporicidal Solution. This sample was tested undiluted and was a mixture of 0.72% $ClO_2$ and 0.4% quaternary ammonium chloride. |
| Test Organisms: | *Clostridium sporogenes* ATCC No. 3584 |
| Method: | The Sporicidal Test Official Final Action as outlined in the Official Methods of Analysis of the Association of Analytical Chemists, Pages 64–65, Eleventh Edition (1970) was followed. The specified time intervals tested were 10, 15 and 30 minutes, 1 and 2 hours |
| Findings: | See attached Table 8 below. |
| Conclusions: | This Cryoclave Sporicidal Solution, when tested undiluted at time intervals of 10, 15 and 30 minutes, 1 hour and 2 hours was sporicidal against *Clostridium sporogenes*. |

TABLE 8

| Specified Contact Intervals | 21 Day Incubation | | Heat Shocked and Reincubated | |
|---|---|---|---|---|
|  | Sub-culture | Resub-culture | Sub-culture | Resub-culture |
| 10 min. | 0/10 | 0/10 | 0/10 | 0/10 |
| 15 min. | 0/10 | 0/10 | 0/10 | 0/10 |
| 30 min. | 0/10 | 0/10 | 0/10 | 0/10 |
| 1 hr. | 0/10 | 0/10 | 0/10 | 0/10 |
| 2 hrs. | 0/10 | 0/10 | 0/10 | 0/10 |

Test Spores in 2.5 N HCl (Organisms Control for viability)
74  2 min. 2/2
5 min. 2/2
10 min. 2/2
20 min. 2/2

Note: Number of positives/total number of specimens

| | |
|---|---|
| Samples: | Cryoclave 20 Sample was received. This sample was identified as: 1. One 1 gallon plastic bottle containing a clear liquid labeled: Cryoclave #20 Sample. The above sample was tested undiluted and was a mixture of 0.72% $ClO_2$ and 0.4% quaternary ammonium chloride. |
| Test Organism: | *Clostridium perfringens* ATCC 13124 |
| Method: | The Sporicidal Test - Official Final Action as outlined in the Official Methods of Analysis of the Association of Official Analytical Chemists, Eleventh Edition (1970) pp. 64–65 was followed. |
| Findings: | See attached Table 9 below |
| Conclusions: | Cryoclave 20 sample when tested undiluted according to the above method using porcelain penicylinders against *Clostridium perfringens* satisfied the requirements of the A. O. A. C. Sporicidal Test. |

Specifically, the four dialkyl quaternary compounds employed with chlorine dioxide in the testing embodiments of the invention, all of which gave outstanding results were:
Octyl-decyl dimethyl ammonium chloride
Didecyl dimethyl ammonium chloride
Didodecyl dimethyl ammonium chloride -continued Octyl-dodecyl dimethyl ammonium chloride

TABLE 9

| Cryoclave 20 Samples | Type of Carriers Employed | No. of Carriers Employed | After 21 Days of Incubation Primary Subcultures | After 21 Days of Incubation Secondary Subcultures | After Heat Shocking and Reincubation Primary Subcultures | After Heat Shocking and Reincubation Secondary Subcultures |
|---|---|---|---|---|---|---|
| 1. Plant Batch #1 6/1/72 | porcelain pencylinders | 30 | 0/30 | 0/30 | 0/30 | 0/30 |
| Test Spores in 2.5 N HCl (Organism Control) | | | | | | |
| | 2 min. 2/2 | | | | | |
| | 5 min. 2/2 | | | | | |

Note: Number of positive/total number of specimens

EXAMPLE 4

Fungicidal Activity

The composition of cold sterilization solution as described in Example 1 was tested against Trichophyton interdigitale ATCC No. 640 as the test organism.

The fungicidal test used was that one outlined in the Official Methods of Analysis of the Association of Official Analytical Chemists, pages 65–66, Eleventh edition (1970).

The results of the testing are shown in Table 10 below.

TABLE 10

| 1:5 (20%) dilution Exposure Time | Subculture | Resubculture | Second Resubculture |
|---|---|---|---|
| 5 min | −, − | −, − | −, − |
| 10 min | −, − | −, − | −, − |
| 15 min | −, − | −, − | −, − |

| 1:32 (4 oz./gallon) Exposure Time | Subculture | Resubculture | Second Resubculture |
|---|---|---|---|
| 5 min | −, − | −, − | −, − |
| 10 min | −, − | −, − | −, − |
| 15 min | −, − | −, − | −, − |
| Control | +, + | +, + | +, + |

+ = Growth
− = No Growth

These tests show that the composition was fungicidal against trichophyton interdigitale at 1:5 (20%) and 1:32 (4 oz./gallon) dilutions.

EXAMPLE 5

Bactericidal Activity

The composition of cold sterilization solution as described in Example 1 was tested for bactericidal activity against Staphylococcus aureus, ATCC No. 6538. The use-dilution method for testing is outlined in the Official Methods of Analysis of the Association of Official Analytical Chemists, pages 61–63, Eleventh Edition (1970).

The results obtained are outlined in Table 11 below.

TABLE 11

| CRYOCLAVE SOLUTION | | |
|---|---|---|
| 1:5 (20%) Dilution | | |
| No. Carriers employed | Tubes Showing Growth Subculture | Tubes Showing Growth Resubculture |
| 20 | 0 | 0 |
| 1:32 (4 oz./gallon) Dilution | | |
| No. Carriers employed | Tubes Showing Growth Subculture | Tubes Showing Growth Resubculture |
| 20 | 0 | 0 |
| Control No. Carriers employed | | |
| 10 | 10 | 10 |

The results demonstrate that the composition was bactericidal against Staphylococcus aureus at 1:5 (20%) and 1:32 (4 oz./gallon) dilutions.

EXAMPLE 6

Oral $LD_{50}$ in Rats

A series of tests was conducted to study the effect of the composition of cold sterilization solution as described in Example 1 when administered orally to rats.

The method employed is described in "Appraisal of the Safety of Chemicals in Foods, Drugs and Cosmetics", published by the Association of Food and Drug Officials of the United States.

The results are reported in detail in Table 12 below. They may be summarized by stating that the oral $LD_{50}$ in rats is 3.30 ml/kg. The 19/20 confidence limits equals 2.66–4.09; the slope is 1.43.

TABLE 12

ORAL $LD_{50}$ - RATS
SOLUTION OF THE DOSE-EFFECT CURVE OF CRYOCLAVE

| Dose ml/kg | Response | Observe % | Expected % | Observed Minus Expected | Contribution to $(CHI)^2$ |
|---|---|---|---|---|---|
| 1 | 0/10 | 0 | 0.0 | 0.0 | 0.0 |
| 2 | 1/10 | 10 | 8.0 | 2.0 | 0.005 |
| 3 | 4/10 | 40 | 40.0 | 0.0 | 0.0 |
| 4 | 7/10 | 70 | 71.0 | 1.0 | 0.0005 |
| 5 | 10/10 | 100(96.2) | 88.0 | 8.2 | 0.0042 |

Total animals = 50     Total 0.0097
Number of Doses, K = 5
$(Chi)^2$ = 0.01 (Total × Number of animals/Number of doses)
Degrees of Freedom, n = k − 2 = 3
$(Chi)^2$ from table 2 for n of 3 = 7.82; 0.01 is less than 7.82, therefore, the data are not significantly heterogeneous
$ED_{84}$ ml/kg. 4.70
$ED_{50}$ ml/kg. 3.30
$ED_{16}$ ml/kg. 2.30

$$S = \frac{ED_{84}/ED_{50} + ED_{50}/ED_{16}}{2} = \frac{1.42 + 1.43}{2} = 1.43$$

N' = 20 (The total number of animals used between 16% to 84% expected effects.

TABLE 12-continued

ORAL $LD_{50}$ - RATS
SOLUTION OF THE DOSE-EFFECT CURVE OF CRYOCLAVE

| Dose ml/kg | Response | Observe % | Expected % | Observed Minus Expected | Contribution to $(CHI)^2$ |
|---|---|---|---|---|---|

$fED_{50} = (S)\ 2.77/\ N' = 1.24$ (from Nomograph No. 2)
$ED_{50} \times fED_{50} = 4.09$
$ED_{50}/\ fED_{50} = 2.66$
 $ED_{50}$ and 19/20 confidence limits: 3.30 (2.66 - 4.09)
R = largest/smallest dose = 2.5
A = 1.17 (from Nomograph No. 3, using S = 1.43 and R = 2.5)
$fS = (A)\ 10(K-1)/K\ N' = 1.32$ (from Nomograph No. 2)
$S \times fS = 1.89$
$S / fS = 1.08$
 S and 19/20 confidence limits: 1.43 (1.08 - 1.89)

Most deaths of the animals occurred within 12–36 hours after gavage. The gross autopsy findings were cloudy liver and kidneys and petechiae throughout the alimentary tract.

EXAMPLE 7

Primary Skin Irritation in Rabbits

The composition was studied to determine its effects as a primary skin irritant in rabbits.

The method used is described in the U.S. Department of Agriculture, Federal Insecticide Fungicide and Rodenticide Act, Section 312,116 of the regulations (7CFR part 362) paragraph (c). The dose is an 0.5 ml/patch with four patches on each of 6 rabbits.

The results obtained are set forth in Table 13 below.

The primary skin irritation index is 2.33. The composition produced both hyperemia and edema in rabbit skins under the conditions of the tests.

TABLE 13

PRIMARY SKIN IRRITATION INDEX - RABBITS
SPORICIDAL FORMULATION "CRYOCLAVE"

| Erythema and eschar formation: | Exposure time Hours | Exposure Unit Value Rabbit 1 | Exposure Unit Value Rabbit 2 | Exposure Unit Value Rabbit 3 | Exposure Unit Value Rabbit 4 | Exposure Unit Value Rabbit 5 | Exposure Unit Value Rabbit 6 |
|---|---|---|---|---|---|---|---|
| Intact skin | 24 | 1 | 1 | 1 | 2 | 2 | 1 |
| " | 72 | 1 | 1 | 1 | 1 | 1 | 1 |
| Abraded skin | 24 | 2 | 2 | 2 | 2 | 2 | 2 |
| " | 72 | 2 | 2 | 2 | 2 | 2 | 2 |
| Subtotal | | 6 | 6 | 6 | 7 | 7 | 6 |
| Edema formation: | | | | | | | |
| Intact skin | 24 | 1 | 1 | 1 | 1 | 1 | 1 |
| " | 72 | 0 | 0 | 0 | 0 | 0 | 0 |
| Abraded skin | 24 | 1 | 1 | 1 | 1 | 1 | 1 |
| " | 72 | 1 | 1 | 1 | 1 | 1 | 1 |
| Subtotal | | 3 | 3 | 3 | 3 | 3 | 3 |
| Total | | 9 | 9 | 9 | 10 | 10 | 9 |
| Average | | 2.25 | 2.25 | 2.25 | 2.5 | 2.5 | 2.25 |
| Overall Average | | 2.33 | | | | | |

EXAMPLE 8

Eye Irritation Tests

The composition was tested for its effects as an eye irritant in rabbits.

The method employed is described in U.S. Department of Agriculture, Federal Insecticide, Fungicide and Rodenticide Act, Section 362, 116 of the regulations (7CFR part 362) paragraph (d).

The dose was 0.1 ml in one eye of each of six rabbits. Results of the tests are tabulated in Tables 14 and 15.

TABLE 14

Findings: Sporicidal Formulation "Cryoclave" Made 1/15/72

| | | Days | | | | | | |
|---|---|---|---|---|---|---|---|---|
| Rabbit #1 | | 1 | 2 | 3 | 4 | 5 | 6 | 7 |
| I. Cornea | | | | | | | | |
| A. Opacity | | 2 | 2 | 2 | 2 | 1 | 1 | 1 |
| B. Area | | 2 | 2 | 2 | 2 | 1 | 1 | 1 |
| A×B×5 | | 20 | 20 | 20 | 20 | 5 | 5 | 5 |
| II. Iris | | | | | | | | |
| A. Values | | 1 | 1 | 1 | 1 | 0 | 0 | 0 |
| ×5 | | 5 | 5 | 5 | 5 | | | |
| III. Conjunctivae | | | | | | | | |
| A. Redness | | 3 | 3 | 3 | 3 | 2 | 2 | 2 |
| B. Chemosis | | 4 | 4 | 3 | 3 | 2 | 2 | 2 |
| C. Discharge | | 3 | 3 | 3 | 3 | 2 | 2 | 2 |
| (A=B=C)×2 | | 20 | 20 | 18 | 18 | 12 | 12 | 12 |
| | Total | 45 | 45 | 43 | 43 | 17 | 17 | 17 |
| Rabbit #2 | | | | | | | | |
| I. Cornea | | | | | | | | |
| A. Opacity | | 2 | 2 | 2 | 2 | 2 | 1 | 1 |
| B. Area | | 2 | 2 | 2 | 2 | 2 | 1 | 1 |
| A×B×5 | | 20 | 20 | 20 | 20 | 20 | 5 | 5 |
| II. Iris | | | | | | | | |
| A. Values | | 1 | 1 | 1 | 0 | 0 | 0 | 0 |
| ×5 | | 5 | 5 | 5 | | | | |
| III. Conjunctivae | | | | | | | | |

TABLE 14-continued
Findings: Sporicidal Formulation "Cryoclave" Made 1/15/72

| | Days | | | | | | |
|---|---|---|---|---|---|---|---|
| A. Redness | 3 | 3 | 3 | 2 | 2 | 2 | 2 |
| B. Chemosis | 4 | 4 | 3 | 2 | 2 | 2 | 2 |
| C. Discharge | 3 | 3 | 3 | 2 | 2 | 2 | 2 |
| $(A=B=C) \times 2$ | 20 | 20 | 18 | 12 | 12 | 12 | 12 |
| Total | 45 | 45 | 43 | 32 | 32 | 17 | 17 |
| Rabbit #3 | | | | | | | |
| I. Cornea | | | | | | | |
| A. opacity | 2 | 2 | 2 | 2 | 1 | 1 | 1 |
| B. Area | 2 | 2 | 2 | 2 | 1 | 1 | 1 |
| $A \times B \times 5$ | 20 | 20 | 20 | 20 | 5 | 5 | 5 |
| II. Iris | | | | | | | |
| A. Values | 1 | 1 | 1 | 0 | 0 | 0 | 0 |
| $\times 5$ | 5 | 5 | 5 | | | | |
| III. Conjunctivae | | | | | | | |
| A. Redness | 3 | 3 | 3 | 2 | 2 | 2 | 2 |
| B. Chemosis | 4 | 4 | 4 | 3 | 2 | 2 | 2 |
| C. Discharge | 3 | 3 | 3 | 2 | 2 | 2 | 2 |
| $(A+B+C) \times 2$ | 20 | 20 | 20 | 14 | 12 | 12 | 12 |
| Total | 45 | 45 | 45 | 34 | 17 | 17 | 17 |

TABLE 15
Findings: Sporicidal Formulation "Cryoclave" Made 1/15/72

| | Days | | | | | | |
|---|---|---|---|---|---|---|---|
| Rabbit #4 | 1 | 2 | 3 | 4 | 5 | 6 | 7 |
| I. Cornea | | | | | | | |
| A. Opacity | 2 | 2 | 2 | 2 | 2 | 1 | 1 |
| B. Area | 2 | 2 | 2 | 2 | 2 | 1 | 1 |
| $A \times B \times 5$ | 20 | 20 | 20 | 20 | 20 | 5 | 5 |
| II. Iris | | | | | | | |
| A. Values | 1 | 1 | 1 | 0 | 0 | 0 | 0 |
| $\times 5$ | 5 | 5 | 5 | | | | |
| III. Conjunctivae | | | | | | | |
| A. Redness | 3 | 3 | 3 | 3 | 3 | 2 | 2 |
| B. Chemosis | 4 | 4 | 3 | 3 | 3 | 2 | 2 |
| C. Discharge | 3 | 3 | 3 | 3 | 3 | 2 | 2 |
| $(A+B+C) \times 2$ | 20 | 20 | 18 | 18 | 18 | 12 | 12 |
| Total | 45 | 45 | 43 | 38 | 38 | 17 | 17 |
| Rabbit #5 | | | | | | | |
| I. Cornea | | | | | | | |
| A. Opacity | 2 | 2 | 2 | 2 | 2 | 1 | 1 |
| B. Area | 2 | 2 | 2 | 2 | 2 | 1 | 1 |
| $A \times B \times 5$ | 20 | 20 | 20 | 20 | 20 | 5 | 5 |
| II. Iris | | | | | | | |
| A. Values | 1 | 1 | 1 | 0 | 0 | 0 | 0 |
| $\times 5$ | 5 | 5 | 5 | | | | |
| III. Conjunctivae | | | | | | | |
| A. Redness | 3 | 3 | 3 | 2 | 2 | 2 | 2 |
| B. Chemosis | 4 | 4 | 3 | 2 | 2 | 2 | 2 |
| C. Discharge | 3 | 3 | 3 | 2 | 2 | 2 | 2 |
| $(A=B-C) \times 2$ | 20 | 20 | 18 | 12 | 12 | 12 | 12 |
| Total: | 45 | 45 | 43 | 32 | 32 | 17 | 17 |
| Rabbit #6 | | | | | | | |
| I. Cornea | | | | | | | |
| A. Opacity | 2 | 2 | 2 | 2 | 2 | 1 | 1 |
| B. Area | 2 | 2 | 2 | 2 | 2 | 1 | 1 |
| $A \times B \times 5$ | 20 | 20 | 20 | 20 | 20 | 5 | 5 |
| II. Iris | | | | | | | |
| A. Values | 1 | 1 | 1 | 0 | 0 | 0 | 0 |
| $\times 5$ | 5 | 5 | 5 | | | | |
| III. Conjunctivae | | | | | | | |
| A. Redness | 3 | 3 | 3 | 3 | 3 | 2 | 2 |
| B. Chemosis | 4 | 4 | 3 | 3 | 3 | 2 | 2 |
| C. Discharge | 3 | 3 | 3 | 3 | 3 | 2 | 2 |
| $(A+B+C) \times 2$ | 20 | 20 | 18 | 18 | 18 | 12 | 12 |
| Total | 45 | 45 | 43 | 38 | 38 | 17 | 17 |

The composition as tested produced corneal and conjunctival irritation which persisted with lessening intensity through the seven day observation period. Iritic irritation was observed in 5 of 6 rabbits through day 3, and in one rabbit through day 4.

What is claimed is:

1. A sporicidal composition which comprises from 1.0 to 6.0% chlorine dioxide and a small amount but effective amount of about 0.2% up to about 2.0% of a quaternary ammonium salt selected from the group consisting of octyl-decyl dimethyl ammonium chloride, didecyl dimethyl ammonium chloride, didodecyl dimethyl ammonium chloride, and octyl-dodecyl dimethyl ammonium chloride.

2. The composition of claim 1 which is an aqueous composition.

3. The composition of claim 1 containing an effective amount of a stabilizer and an effective amount of an emulsifier.

4. The composition of claim 1 containing an effective amount of a stabilizer and an effective amount of a primary alcohol ethoxylate emulsifier having 12 moles of ethylene oxide and selected from the group consisting of those having the primary alcohol portion derived from $C_{12}$, $C_{13}$, $C_{14}$ and $C_{15}$ primary alcohols.

5. The composition of claim 1 in which the quaternary ammonium salt is di-decyl dimethyl ammonium chloride.

6. The composition of claim 1 in which the quaternary ammonium salt is di-dodecyl dimethyl ammonium chloride.

7. The composition of claim 1 in which the quaternary ammonium salt is octyl-dodecyl dimethyl ammonium chloride.

8. The composition of claim 1 in which the quaternary ammonium salt is octyl decyl-dimethyl ammonium chloride.

9. A method of killing spores on hard surfaces which comprises contacting said surfaces with a sporicidally effective amount of a composition which comprises from 0.1 to 6.0% chlorine dioxide and a small but effective amount of about 0.2% up to about 2.0% of a quaternary ammonium salt selected from the group consisting of octyl-decyl dimethyl ammonium chloride, didecyl dimethyl ammonium chloride, didodecyl dimethyl ammonium chloride, and octyl-dodecyl dimethyl ammonium chloride.